United States Patent
Huang

(10) Patent No.: US 9,351,931 B2
(45) Date of Patent: May 31, 2016

(54) PHARMACEUTICAL PREPARATION FOR TUMOR CHEMOTHERAPY AND METHOD FOR PRODUCING THE SAME

(71) Applicants: HUBEI SOUNDNY BIOTECHNOLOGY CO., LTD., Wuhan (CN); Bo Huang, Wuhan (CN)

(72) Inventor: Bo Huang, Wuhan (CN)

(73) Assignees: HUBEI SOUNDNY BIOTECHNOLOGY CO., LTD., Hubei (CN); Bo Huang, Hubei (CN)

( * ) Notice: Subject to any disclaimer, the term of this patent is extended or adjusted under 35 U.S.C. 154(b) by 51 days.

(21) Appl. No.: 13/986,150

(22) Filed: Apr. 5, 2013

(65) Prior Publication Data
US 2013/0236537 A1     Sep. 12, 2013

Related U.S. Application Data

(63) Continuation of application No. PCT/CN2012/070609, filed on Jan. 19, 2012.

(51) Int. Cl.
| | |
|---|---|
| A61K 9/127 | (2006.01) |
| A61K 45/06 | (2006.01) |
| A61K 9/00 | (2006.01) |
| A61K 9/50 | (2006.01) |
| A61K 31/519 | (2006.01) |
| A61K 31/704 | (2006.01) |
| A61K 33/24 | (2006.01) |
| A61K 35/13 | (2015.01) |

(52) U.S. Cl.
CPC .............. *A61K 9/127* (2013.01); *A61K 9/0019* (2013.01); *A61K 9/5068* (2013.01); *A61K 9/5089* (2013.01); *A61K 31/519* (2013.01); *A61K 31/704* (2013.01); *A61K 33/24* (2013.01); *A61K 35/13* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2004/0028692 A1 | 2/2004 | Zitvogel et al. ............ 424/184.1 |
| 2011/0070292 A1* | 3/2011 | Javeri et al. ................ 424/450 |

FOREIGN PATENT DOCUMENTS

| | | | |
|---|---|---|---|
| CN | 102302784 A | | 1/2012 |
| EP | 2 450 032 A2 | | 5/2012 |
| WO | WO-95-20424 | * | 3/1995 |
| WO | WO-99-58645 | * | 11/1999 |
| WO | WO2011/062244 A1 | | 5/2011 |
| WO | 2011/002239 A2 | | 6/2011 |

OTHER PUBLICATIONS

Kremer JMH, Vesicles of variable diameter prepared by a modified injection method, Biochemistry, 16(17), 1977, 3932-3935.*
Shin H, Sodium butyrate-induced DAPK-mediated apoptosis in human gastric cancer cells, 2012, 1111-1115.*
Tang, KE et al., "Delivery of chemotherapeutic drugs in tumour cell-derived microparticles" Nature Communication 3, Article No. 1282, pp. 1-11 | Published Dec. 18, 2012.
International Search Report of International Application No. PCT/CN2012/070609, dated May 24, 2012.
Chinese First Examination Report of China Application No. 201110241369.8, dated May 22, 2012.
Chinese Notice of Issurance of China Application No. 201110241369.8, dated Sep. 25, 2012.
Jianguo MA et al., "Cells Designed to Deliver Anticancer Drugs by Apoptosis" Cancer Research, Mar. 2002, vol. 62, pp. 1382-1387.
The extended European Search Report of corresponding International PCT Application No. PCT/CN2012/070609 and corresponding European Application No. 12825203.8, dated Aug. 25, 2014.

* cited by examiner

*Primary Examiner* — Frederick Krass
*Assistant Examiner* — Celeste A Roney
(74) *Attorney, Agent, or Firm* — J.C. Patents

(57) ABSTRACT

The present invention provides a pharmaceutical preparation for tumor chemotherapy and a method for producing the same, the pharmaceutical preparation for tumor chemotherapy comprises cell vesicles derived from apoptotic tumor cells and chemotherapeutic drugs as active ingredients wrapped within the cell vesicles. The chemotherapeutic drugs contained within the pharmaceutical preparation are chemotherapeutic drugs containing active ingredients for the treatment of the tumors from which the cell vesicles are provided. The present invention also provides a method for producing the pharmaceutical preparation for tumor chemotherapy. The technical solutions provided by the present invention can selectively release the chemotherapeutic drugs to the tumor sites and maintain lasting medicinal effect, increasing their killing effects against tumor cells and reducing the toxic side-effect of the chemotherapeutic drugs to normal cells.

8 Claims, 6 Drawing Sheets
(3 of 6 Drawing Sheet(s) Filed in Color)

PHARMACEUTICAL PREPARATION FOR TUMOR CHEMOTHERAPY AND METHOD FOR PRODUCING THE SAME

CROSS-REFERENCE TO RELATED APPLICATIONS

This application is a continuation of International Application No. PCT/CN2012/070609, filed on Jan. 19, 2012, which claims priority to Chinese Patent Application No. 201110241369.8, filed on Aug. 22, 2011, both of which are hereby incorporated by reference in their entireties.

FIELD OF TECHNOLOGY

The present invention relates to a pharmaceutical preparation and a method for producing the same, and particularly to a pharmaceutical preparation for tumor chemotherapy and a method for producing the same.

BACKGROUND

In recent years, tumor has become a type of disease severely endangering people's life, its treatment has become a subject to which numerous scientific researchers are dedicated. Using chemical drugs (chemotherapeutic drugs) to eliminate tumor cells is a very important and conventional means in the treatment of tumorous diseases, however, the application of chemotherapeutic drugs would kill normal tissue cells while killing tumor cells, not only bringing unbearable side-effects to patients, but often times also resulting in the failure of chemotherapy.

That chemotherapeutic drugs would kill normal cells of the organism is the essence for the toxic side-effects of chemotherapeutic drugs. In order to avoid the nonspecific kill caused by chemotherapeutic drugs to the normal cells, the existing solution is wrapping the chemotherapeutic drugs into carriers, so that the drugs can be selectively released in the tumor sites, even into tumor cells to kill the tumor cells. One of the common carriers is microparticle carrier system made of nano-materials, the nano-materials that have been reported can be used to wrap chemotherapeutic drugs so as to perform a targeted drug delivery include: polyethylene glycol-phosphatidyl ethanolamine copolymer (PEG-PE), poly(lactic-co-glycolic acid) (PLGA) and so on, which have been proven to be used to wrap chemotherapeutic drugs, and deliver the chemotherapeutic drugs to the tumor sites, such that the killing effect of chemotherapeutic drugs to tumor cells can be enhanced. However, since nano-materials are exogenous substances which have a certain toxic side-effects to a living organism in themselves, and nano particles in particle sizes and specifications provided for clinical use also make them easily pass through the cell membrane of normal cells, which increases the toxic side-effects of the nano carriers and the chemotherapeutic drugs they carried therein to the organism. In addition, the special materials and processing technology adopted by some nano particles greatly increase the cost, and not conducive to clinical application.

Therefore, how to decrease toxic side-effects of the chemotherapeutic drugs targetedly, but not decrease or even increase its killing effect against tumor cells, has become a difficult problem to be solved urgently in the field of tumor research.

SUMMARY

The present invention provides a pharmaceutical preparation for tumor chemotherapy, taking cell vesicles derived from apoptotic tumor cells as the carriers of the pharmaceutical preparation for tumor chemotherapy, which wrap chemotherapeutic drugs to form the preparation, and as a targeted drug, it is more conductive for the chemotherapeutic drugs to reach the tumor sites for treatment, improving their medicinal effect, while overcoming the defects that the administration the chemotherapeutic drugs through exogenous carriers has toxic side-effects to the organism.

The present invention also provides a method for producing a pharmaceutical preparation for tumor chemotherapy, wherein chemotherapeutic drugs acting as active therapeutic ingredients can be wrapped into cell vesicles derived from the apoptotic tumor cells.

The present invention also provides a method for the treatment of tumors, through which the tumor cells can be effectively killed while the toxic side-effects of the chemotherapeutic drugs to organism can be reduced.

A pharmaceutical preparation for tumor chemotherapy provided by present invention comprises: cell vesicles derived from the apoptotic tumor cells and chemotherapeutic drugs acting as active ingredients wrapped within the cell vesicles.

As basic knowledge of the field, a cell is composed of a cell membrane and cellular content wrapped therein, while the cell membrane is composed of phospholipid bilayer and protein molecules embedded therein, whose spherical structure is maintained by the centripetal pulling force formed by the protein fibrils within the cell, which are called cytoskeleton. When a cell is subject to the stimulus of external signals (for example: chemotherapeutic drugs or UV light) apoptosis occurs, some protein fibrils of the cytoskeleton attached to the cell membrane part are broken, or lose adhesion, and their centripetal pulling force suddenly disappeared, such that the local cell membrane structure expands outward under the effect of the outgoing pulling force, and protrudes with cellular content wrapped therein, is released to the sub-hierarchical structure between the cell and molecules in the form of cell vesicles, whose size is mostly between 100-1000 nanometers (nm), that is the "cell vesicles" as described in this invention. Since adopting the above cell vesicles as carriers for wrapping the chemotherapeutic drugs, the pharmaceutical preparation provided by the present invention can act as a kind of micro-particles, more conductive to pass through tumor capillaries to kill the tumor cells as a targeted drug (for tumors in general, the gap between the cells which constitute the blood vessels of the tumors will significantly increase, compared with the gap between the cells of normal tissues, reaching 100-780 nm in size) rather than enter normal tissues (their permeability usually is 5-10 nm) thus will not cause any damage to normal tissues, and avoid toxic effects to organism that were caused by the targeted drugs composed of exogenous carriers such as nano-materials.

The preparation obtained by wrapping chemotherapeutic drugs within cell vesicles derived from apoptosis of tumor cells according to the present invention, compared with the chemotherapeutic drugs of using exogenous carriers, is more conductive to investigate the medicinal effects and to reduce drug-resistant of the organism. Since the cell vesicles used for wrapping chemotherapeutic drugs are derived from tumor cells, the recommended tumor cells are those of the same type of the tumor cells to be treated, whose cell vesicles can be easily integrated with the cell membrane of the tumor cells of a patient's body, interfere with the original pump system in the cell membrane of the tumor cells and reduce the pump-out of the chemotherapeutic drugs having entered into the tumor cells by the pump system, thereby enhancing the sensitivity of the tumor cells against chemotherapeutic drugs which are wrapped within the cell vesicles.

Besides, when the cell vesicles wrapping certain dose of chemotherapeutic drugs are administrated to the tumor cells, "chain reactions" occur: that is, after the micro-particles with the chemotherapeutic drugs wrapped therein killing the tumor cells that the micro-particles have previously entered, the apoptotic tumor cells induced by the killing of chemotherapeutic drugs continue to form new cell vesicles wrapping the chemotherapeutic drugs, and administration of the chemotherapeutic drugs to other tumor cells continues until the medicinal effects of the chemotherapeutic drugs are fully released. It can be understood that, compared with administrating chemotherapeutic drugs directly, the micro-particles wrapping the same dose of chemotherapeutic drugs have a much more significant killing effect against the tumor cells. Therefore, in the treatment of tumor, to achieve the same therapeutic effect of direct administration of chemotherapeutic drugs, the dosage of the pharmaceutical preparation for tumor chemotherapy of the present invention can be appropriately reduced, or a preparation with a smaller specification of chemotherapeutic drug amount wrapped within the cell vesicles can be selected as required, thereby to a certain extent, the usage amount of chemotherapeutic drugs can be reduced, which also allow the chemotherapeutic drugs to fully investigate the medicinal effects on the body and to avoid deposition, so as to reduce the damage caused by chemotherapeutic drugs on human body.

Actually, the present invention provides a new way and solution for obtaining a targeted drug, the specific chemotherapeutic drugs in the composition of the targeted drug can be chemotherapeutic drugs used in the treatment for various types of tumors of clinical trials, such as: chemotherapeutic drugs for ovarian tumor, breast tumor, lung tumor, stomach tumor, colon tumor, liver tumor, bladder tumor, leukemia and/or glioma, it can be one chemotherapeutic drug or a combination of chemotherapeutic drugs, and the cell vesicles (the drug carriers) used to wrap the chemotherapeutic drugs can be derived from the same type of tumor cells that are to be treated.

According to an embodiment for the pharmaceutical preparation of the present invention, the chemotherapeutic drug contained in the pharmaceutical preparation is a chemotherapeutic drug containing the active ingredients for the treatment of the tumors from which the cell vesicles are provided; the chemotherapeutic drug contained also can be drugs which have already been used in clinical trials, such as injection preparation or oral preparation, if it is in the form of tablet, powder or granules, they can be dissolved for usage (i.e., after being dissolved, the chemotherapeutic drug is incubated with cell vesicles so as to be wrapped into the cell vesicles).

The pharmaceutical preparation of the present invention can be a conventional preparation form of targeted drugs, such as injection preparation.

In an embodiment of the present invention, the granularity of the pharmaceutical preparation for tumor chemotherapy formed by wrapping the chemotherapeutic drug within the cell vesicles is 100-1000 nm. The dosage of the chemotherapeutic drug contained in the pharmaceutical preparation for tumor chemotherapy is controlled by the amount of the chemotherapeutic drug added to the tumor cell-culture medium during the preparation process, but the maximum dosage depends on the maximum saturation of the adopted chemotherapeutic drug in the cell vesicles which act as carriers. Therefore, within the highest dosage range, pharmaceutical preparations of different specifications can be obtained.

The present invention also provides a method for producing the pharmaceutical preparation, that is, the chemotherapeutic drug is wrapped into the cell vesicles through any suitable means and the cell vesicles for use are obtained by inducing the apoptosis of tumor cells.

According to an embodiment of the present invention, the method for producing pharmaceutical preparation for tumor chemotherapy provided by the present invention, comprises:

administrating a chemotherapeutic drug as active ingredient to tumor cells to induce apoptosis of tumor cells, and collecting the micro-particles released from the apoptotic tumor cells, wherein the micro-particles are the pharmaceutical preparation formed after wrapping the chemotherapeutic drugs within the cell vesicles; or using UV to irradiate the tumor cells to induce apoptosis of tumor cells, collecting the cell vesicles released by the apoptotic tumor cells, then incubating the cell vesicles with the chemotherapeutic drug acting as active ingredient, wrapping the chemotherapeutic drug within the cell vesicles, and collecting micro-particles, wherein the micro-particles are the pharmaceutical preparation formed after wrapping the chemotherapeutic drug within the cell vesicles.

The pharmaceutical preparation can be produced into any desired preparation forms according to conventional drug preparation methods, which can be injection preparation, such as injection liquid.

According to the preparation method of the present invention, pharmaceutical preparations of different specification (the content of active ingredients) can be obtained by controlling the addition amount of chemotherapeutic drug, which facilitates the administration of the pharmaceutical preparation for the tumor patients in different phases of the disease. The content of chemotherapeutic drug in the obtained micro-particles can be determined in accordance with the nature of the selected drug, the type of the tumor that provide cell vesicles, as well as the disease phase of the tumor patients to be treated by proper trials. In general, the amount of chemotherapeutic drug contained within the pharmaceutical preparation for tumor chemotherapy can be controlled to the amount close to the maximum saturation of the chemotherapeutic drug in the cell vesicles which act as carriers, or the addition amount of chemotherapeutic drug can be controlled by predetermined specification of the pharmaceutical preparation.

Based on this disclosure, those skilled in the art also can select a proper method for the apoptosis of tumor cells, the method of collecting micro-particles, and the method of collecting the cell vesicles, and the conditions such as the proportion between the cell vesicles and the chemotherapeutic drugs used for treating tumors, according to different types of tumors to be treated, as well as different active ingredients of the chemotherapeutic drugs, so long as the finally obtained cell vesicles with chemotherapeutic drugs acting as active ingredients wrapped therein can exert the desired therapeutic effect. In an embodiment of the present invention, UV or chemotherapeutic drugs is used to induce the apoptosis of tumor cells, and as for the collection of cell vesicles, a supercentrifuge can be used for separation at low temperature or room temperature. The cell vesicles can be collected via a supercentrifuge at low temperature (4° C. or so) and at centrifugal force of 100-100,000 g. Similarly, the collection for micro-particles can also be conducted at low temperature using a supercentrifuge. The micro-particles can be collected via a supercentrifuge at low temperature (4° C. or so) and at centrifugal force of 100-100,000 g. For the incubation of the cell vesicles (obtained by radiating the tumor cells via UV) with the chemotherapeutic drugs, chemotherapeutic drugs are added to the cell vesicles by an amount close to the maximum saturation of the chemotherapeutic drugs within the cell vesicles acting as carriers, and incubated at room temperature to be wrapped within the cell vesicles.

The collected micro-particles can be processed into pharmaceutical preparation in accordance with conventional methods, in particular, injection preparation, for example, injection liquid, which can be produced by suspending the micro-particles with physiologic saline.

The method provided by the present invention for producing pharmaceutical preparation for tumor chemotherapy also comprises culturing tumor cells before inducing the apoptosis of the tumor cells. The tumor cells comprise cells of ovarian tumor, breast tumor, lung tumor, stomach tumor, colon tumor, liver tumor, bladder tumor, leukemia, and/or glioma. The culture method for the above cells can adopt the conventional culture method in the culture field.

A method for the treatment of tumors provided by the present invention, comprising performing chemotherapy through the administration of the pharmaceutical preparation for tumor chemotherapy as described to the patients with tumors.

Further, the chemotherapeutic drugs contained within the pharmaceutical preparation are chemotherapeutic drugs that contain active ingredients for treating the tumors from which the cell vesicles are provided.

The chemotherapeutic pharmaceutical preparation provided by the present invention can be administrated according to conventional clinical treatment methods, for example, the chemotherapeutic pharmaceutical preparation can be directly administrated by intraperitoneal injection for the tumors of ovarian tumor, the chemotherapeutic pharmaceutical preparation can be targetedly administrated to the tumors of bladder tumor via intravesical instillation through the urethra, the administration dosage can be the same as or lower than the conventional dosage of the chemotherapeutic drugs.

The apoptosis of tumor cells by inducement as described in the present invention, can be judged by the criteria commonly-known by those skilled in the art, such as if the tumor cells become smaller and dimmer through observation, the cells are considered to be apoptotic cells; Incubating the cell vesicles with chemotherapeutic drugs so as to wrap the chemotherapeutic drugs within the cell vesicles can be achieved by standing the cell vesicle system to which chemotherapeutic drugs are added for 2-4 hours at room temperature.

The "chemotherapeutic drugs" wrapped in the cell vesicles as described in the present invention can be the chemotherapeutic drugs which have already been applied to clinical trials prior to the present invention, or the active ingredients of the chemotherapeutic drugs which have already been applied to clinical trials prior to the present invention (can be free or not free of drug excipients), that is, in the process of producing the preparation of the present invention, various commercially available drugs which have already been used to clinical application, or the active ingredients contained within these clinical drugs can be used directly. Therefore, the drug dosage involved in the present invention should be understood as the content of active ingredients in the drug.

The technical solutions of the present invention have the following technical effects:

1. The cell vesicles derived from tumor cells are used as carriers for the pharmaceutical preparation for tumor chemotherapy of the present invention, which solves the problem of toxic side-effects against organism caused by the administration of foreign carriers, and makes the chemotherapeutic drugs acting as active ingredients be selectively released at the tumor sites. Therefore, the toxic side-effects of the chemotherapeutic drugs to normal cells are reduced while increasing the killing effect of the chemotherapeutic drugs to tumor cells.

2. When the pharmaceutical preparation for tumor chemotherapy is administrated to the tumor cells, "chain reactions" occur: the tumor cells which are killed to become apoptotic cells continue to form new cell vesicles wrapping the chemotherapeutic drugs, and administration of the chemotherapeutic drugs to other tumor cells continues until the medicinal effects of the chemotherapeutic drugs are fully released, such that the dosage of chemotherapeutic drugs can be reduced in the treatment, and the damage of chemotherapeutic drugs to human body can be reduced.

3. The method for producing the pharmaceutical preparation for tumor chemotherapy provided by the present invention comprises making the chemotherapeutic drugs well wrapped in cell vesicles, which provides a tumor chemotherapeutic drug with better targeting, and is conductive to increase the killing effect of the chemotherapeutic drugs to tumor cells.

4. Tumor cells have the feature of indefinite proliferation, and their culture methods are mature, in accordance with the technical solution recorded in the present invention, a plenty of cell vesicles can be obtained from tumor cells and can be used for producing the pharmaceutical preparation for tumor chemotherapy of the present invention, the cost is low and the operation is simple.

5. The administration of the pharmaceutical preparation for tumor chemotherapy to the patients achieves the effects of effectively killing the tumor cells while reducing the toxic side-effects of the chemotherapeutic drugs against organism, and is conductive to improve the effects of tumor treatment.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

DETAILED DESCRIPTION

Figure 1:
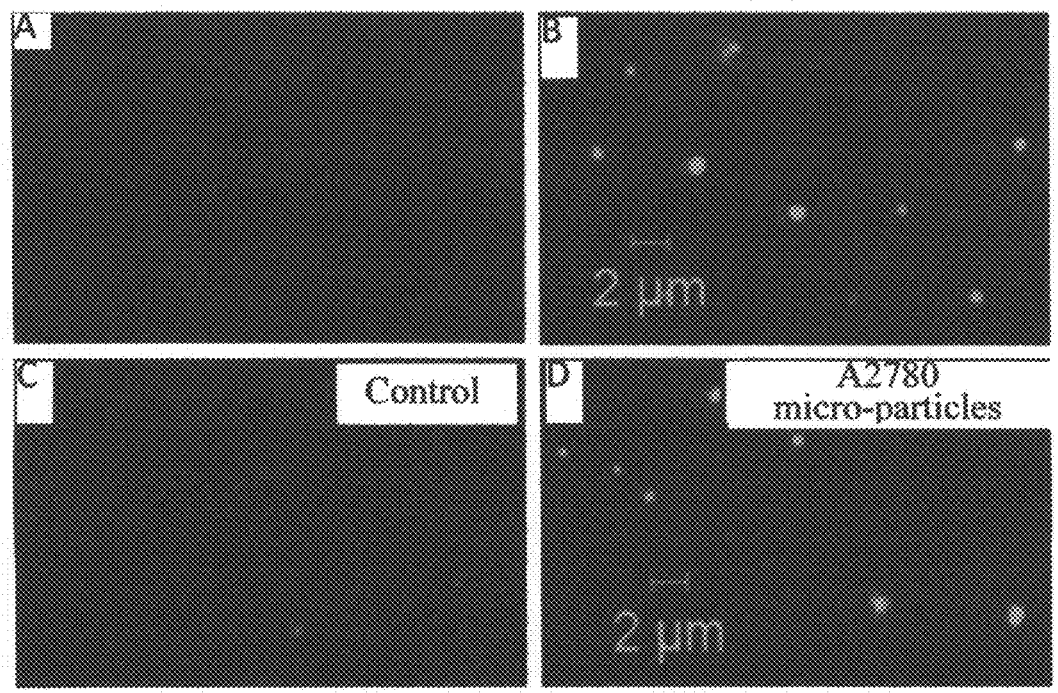
FIG. 1 shows that the micro-particles (cell vesicles with chemotherapeutic drugs wrapped therein) are produced after the tumor cells are treated with chemotherapeutic drugs.

In order to prove the cell vesicles derived from tumor cells can wrap chemotherapeutic drugs therein, and effectively kill the tumor cells without producing any obvious toxic side-effects on the body, the present invention is further described in details in combination with figures and embodiments in the following.

The "cell vesicles" used in the present invention are generated from the apoptotic tumor cells, which have not wrapped chemotherapeutic drugs yet, while the "micro-particles" are formed after the cell vesicles have wrapped the chemotherapeutic drugs therein.

A variety of tumor cells, drugs and test animals used in the following embodiments:

H22 mouse hepatoma cells, A2780 human ovarian carcinoma cells, human breast tumor cell line MCF-7, human lung carcinoma cells A549, human gastric tumor cell line SNU1, human colonic tumor Caco-2, human hepatoma cell line HepG2, human bladder tumor cell line T24, human leukemia cell line K562, as well as human glioma cell line U251, all are commercially available from the ATCC company of the United States or China Center for Type Culture Collection (CCTCC).

50 BALB/c mice, purchased from Laboratory Animal Center, College of Medicine of Wuhan University, each weighing about 18 grams; and 40 SCID mice with severe combined immunodeficiency disease purchased from Laboratory Animal Center, College of Medicine of Wuhan University, each weighing about 18 grams;

Adriamycin, carboxyfluorescein succinimidyl ester (CFSE), PKH26 purchased from Sigma company, and methotrexate, cisplatin purchased from Tongji Hospital Affiliated to Tongji Medical College (Wuhan).

Example 1

Use a Chemotherapeutic Drug to Induce the Apoptosis of Mouse Hepatoma Cells and Human Ovarian Carcinoma Cells Such that Micro-Particles are Produced (Cell Vesicles with Chemotherapeutic Drugs Wrapped Therein are Formed)

1. Experimental Materials and Reagents

H22 mouse hepatoma cells, A2780 human ovarian carcinoma cells, and adriamycin (a chemotherapeutic drug which is commercially available, and commonly used as clinical chemotherapeutic drug, with a red fluorescence).

2. Experimental Procedures

1) H22 mouse hepatoma cells are cultured in Dulbecco Modified Eagle Medium (DMEM), so that the cell amount reaches $2 \times 10^7$; and A2780 human ovarian carcinoma cells are cultured, so that the cell amount reaches $2 \times 10^7$; the above cell-culture medium of H22 mouse hepatoma cells is divided into two groups, each containing half of the cell amount of H22 mouse hepatoma cells; similarly, the cell-culture medium of the A2780 human ovarian carcinoma cells is divided into two groups, each containing half of the cell amount of A2780 human ovarian carcinoma cells.

2) On the first day, adriamycin is administrated to the first group of H22 mouse hepatoma cells (with cell-culture medium), the final concentration of adriamycin is 100 μg/mL in the cell-culture medium; the second group of H22 mouse hepatoma cells (with cell-culture medium) are left untreated;

Adriamycin is administrated to the first group of A2780 human ovarian carcinoma cells (with cell-culture medium), the final concentration of adriamycin is 100 μg/mL in the cell-culture medium; the second group of A2780 human ovarian carcinoma cells (with cell-culture medium) are left untreated.

3) 48 hours after administrating the adriamycin, the first group of H22 mouse hepatoma cells and the first group of A2780 human ovarian carcinoma cells become significantly smaller and dimmer, thus it can be considered that the tumor cells have became apoptotic tumor cells due to drug inducement. The two groups of apoptotic tumor cells are separated, respectively, to obtain the supernatant, which is centrifuged step by step respectively, i.e., centrifuged at the rotational speed of 500 rpm, 1000 rpm, 5000 rpm, respectively, each for 10 minutes, then centrifuged at the centrifugal force of 14000 g for 1 minute to remove cells and debris, the obtained supernatant after the above centrifugation is further centrifuged at the centrifugal force of 14000 g for 1 hour, the micro-particles derived from the apoptosis of the first group of H22 mouse hepatoma cells and the first group of A2780 human ovarian carcinoma cells are obtained respectively, and used as a test group; conduct the same centrifugation steps for the second group of H22 mouse hepatoma cells and the second group of A2780 human ovarian carcinoma cells, to obtain cell vesicles (the control groups will release a small amount of cell vesicles due to the death of cells even under normal culture conditions), and used as a control group.

3. Experimental Results

The micro-particles of the test group and the cell vesicles of the control group above are respectively resuspended with 0.9% (g/ml) physiological saline, and then observed under the two-photon fluorescence microscope after being smeared on a test sheet, respectively. It can be seen from FIG. 1A-FIG. 1D that, as a control group, the cell vesicles from the second group of H22 mouse hepatoma cells into which no adriamycin is administrated did not show red color (see FIG. 1A), and the smear of the cell vesicles from the second group of A2780 human ovarian carcinoma cells into which no adriamycin is administrated also did not show red color after observation (see FIG. 1C); as a test group, the micro-particles derived from the first group of H22 mouse hepatoma cells into which the adriamycin is administrated, red micro-particles can be observed after smearing (see FIG. 1B), the micro-particles derived from the first group of A2780 human ovarian carcinoma cells into which the adriamycin is administrated, red micro-particles can be observed after smearing (see FIG. 1D), since a single adriamycin molecule is too small to be observed with the fluorescence microscope unless being gathered together after being wrapped. The red color observed under the fluorescence microscope is the red light emitted by the cell vesicles in which the chemotherapeutic drugs of adriamycin are wrapped, from which it can be perceived that after the tumor cells being treated with the chemotherapeutic drug, micro-particles of about 1-μm in size are formed by wrapping the chemotherapeutic drugs into cell vesicles, which proves that the cell vesicles have wrapped the chemotherapeutic drugs therein.

Example 2

Use UV to Induce the Apoptosis of Mouse Hepatoma Cells and Human Ovarian Carcinoma Cells, Respectively, to Produce the Cell Vesicles, which are Incubated with the Chemotherapeutic Drugs to Obtain the Micro-Particles with Chemotherapeutic Drugs Wrapped Therein 1. Experimental Materials and Reagents H22 mouse hepatoma cells and A2780 human ovarian carcinoma cells used in example 2 are the same as example 1, the UV device belongs to a conventional cell clean bench, and the adriamycin is the same as example 1.

2. Experimental Procedures

1) H22 mouse hepatoma cells and A2780 human ovarian carcinoma cells are cultured, so that their cell amount reaches $2 \times 10^7$, respectively, the culture method is the same as example 1. The above cell-culture medium of H22 mouse hepatoma cells is divided into two groups, each group containing half of the cell amount of H22 mouse hepatoma cells, similarly, the cell-culture medium of A2780 human ovarian carcinoma cells is divided into two groups, each group containing half of the cell amount of A2780 human ovarian carcinoma cells.

2) On the first day, both the H22 mouse hepatoma cells (with cell-culture medium) and the A2780 human ovarian carcinoma cells (with cell-culture medium) are exposed to UV radiation for 30 minutes.

3) 48 hours after the UV radiation, all the H22 mouse hepatoma cells and all the A2780 human ovarian carcinoma cells become significantly smaller and dimmer, confirming that these tumor cells have been induced by UV to become apoptotic cells. The supernatant of the cell-culture medium of the two types of apoptotic tumor cells are centrifuged step by step, respectively, the method is the same as example 1, the cell vesicles derived from tumor cells of the two types are obtained, respectively.

4) The cell vesicles derived from the first group of H22 mouse hepatoma cells and the first group of A2780 human ovarian carcinoma cells are separately resuspended with 0.9% (g/ml) physiological saline, then into which adriamycin is added, respectively, until reaching a final concentration of 200 μg/mL, and then incubation is conducted for 2 hours at room temperature, after that, centrifugation is conducted at the centrifugal force of 14000 g for 1 hour, to obtain the micro-particles (the cell vesicles with chemotherapeutic drugs wrapped therein) as a test group; the cell vesicles obtained from the second group of H22 mouse hepatoma cells and the second group of A2780 human ovarian carcinoma cells are left untreated, as a control group.

3. Experimental Results

Figure 2:
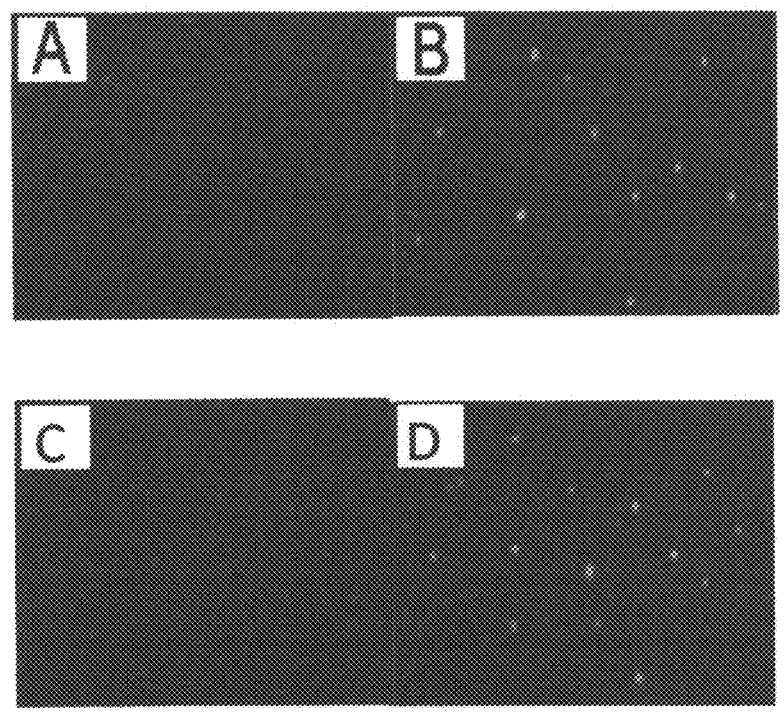
FIG. 2 shows that, after the UV treatment of tumor cells, the released cell vesicles are incubated with the chemotherapeutic drugs to produce micro-particles.

The micro-particles of the test group and the cell vesicles of the control group above are separately resuspended with 0.9% (g/ml) physiological saline, and then observed under the two-photon fluorescence microscope after being smeared on a test sheet, respectively. It can be seen from FIGS. 2A-2D that, as a control group, the cell vesicles derived from the second group of H22 mouse hepatoma cells into which no adriamycin is administrated did not show red color (see FIG. 2A), and the test sheet smeared with the cell vesicles from the second group of A2780 human ovarian carcinoma cells into which no adriamycin is administrated also did not show red color upon observation (see FIG. 2C); as a test group, the micro-particles derived from the first group of H22 mouse hepatoma cells into which the adriamycin is administrated, red micro-particles can be observed after being smeared on a test sheet (see FIG. 2B), in the micro-particles derived from the first group of A2780 human ovarian carcinoma cells into which the adriamycin is administrated, red micro-particles can be observed after being smeared on a test sheet (see FIG. 2D), which proves that after the treatment of UV, the tumor cells release cell vesicles whose size is of about 1 μm, after incubated with the chemotherapeutic drugs, the cell vesicles with chemotherapeutic drugs (refer to relevant explanations within example 1) wrapped therein become the micro-particles as indicated in the Figures.

Example 3

The Cell Vesicles Produced by Inducing the Mouse Hepatoma with UV Radiation can be Absorbed by the Mouse Hepatoma Cells 1. Experimental Materials and Reagents H22 mouse hepatoma cells and the UV device used in example 3 are the same as example 1, carboxyfluorescein succinimidyl ester (CFSE) (green fluorescent dye, commercially available), NCH 26 (red fluorescent dye, commercially available).

2. Experimental Procedures

1) H22 mouse hepatoma cells with a cell amount of $2 \times 10^7$ are cultured, and the culture method is the same with example 1, the above cultured H22 mouse hepatoma cells are divided into two groups with same cell amount.

2) The first group of cells are marked with green fluorescent dye CFSE according to conventional methods.

Figure 3:
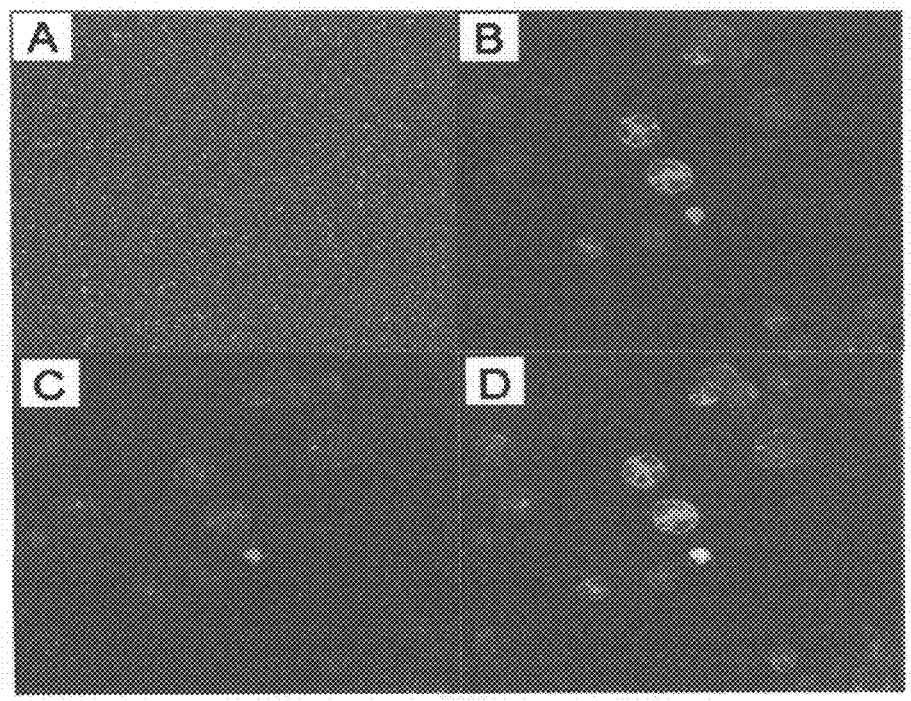
FIG. 3 shows that UV is used to induce the hepatoma cell lines of mice to produce cell vesicles, which can be absorbed by the hepatoma cells of mice.

The cells of the second group are marked with red fluorescent dye PKH26 according to conventional methods, and the marked H22 mouse hepatoma cells show red fluorescence (see FIG. 3B).

3) On the first day, the cells of the above first group marked with green fluorescent dye are exposed to UV radiation for 30 minutes.

4) 48 hours after the UV radiation, H22 mouse hepatoma cells of the first group become significantly smaller and dimmer, and the supernatant of the cell-culture medium of the mouse hepatoma cells is centrifuged step by step, the method is the same as example 1, the cell vesicles derived from mouse hepatoma cells are obtained, and the cell vesicles show green fluorescence (see FIG. 3A).

5) The cell vesicles obtained from the above separation, which are derived from the first group of H22 mouse hepatoma cells with green fluorescence, are incubated with the second group of H22 mouse hepatoma cells with red fluorescence.

3. Experimental Results

After the cell vesicles with green fluorescence are incubated with H22 mouse hepatoma cells with red fluorescence for 4 hours, the mouse hepatoma cells are washed for 3 times and then observed under the fluorescence microscope after being smeared on a test sheet. It can be seen that the cell vesicles with green fluorescence have entered the mouse hepatoma cells with red fluorescence (see FIG. 3C), furthermore, the red fluorescence and the green fluorescence are overlapped to show yellow color (see FIG. 3D), which proves that the cell vesicles can be absorbed by the tumor cells.

Example 4

The Micro-Particles (Formed by Wrapping the Chemotherapeutic Drugs within the Cell Vesicles) Produced by Inducing the Mouse Hepatoma Cell Line with Chemotherapeutic Drugs have Significant Killing Effect Against the Mouse Hepatoma Cells after being Absorbed 1. Experimental Materials and Reagents H22 mouse hepatoma cells and A2780 human ovarian carcinoma cells used in example 4 are the same with example 1, and the chemotherapeutic drugs of methotrexate, cisplatin are commercially available.

2. Experimental Procedures

1) H22 mouse hepatoma cells and A2780 human ovarian carcinoma cells are cultured, so that the cell amount reaches $3 \times 10^7$, respectively, and the culture method is the same as example 1, the obtained cell-culture medium of H22 mouse hepatoma cells is divided into three groups, each containing ⅓ cell amount of H22 mouse hepatoma cells; similarly, the cell-culture medium of the A2780 human ovarian carcinoma cells is divided into three groups, each containing ⅓ cell amount of A2780 human ovarian carcinoma cells.

2) on the first day, 1 ml $5 \times 10^6$ H22 mouse hepatoma cells are taken out from the first group of H22 mouse hepatoma cells and into which 10 μg chemotherapeutic drug of methotrexate is administrated; at the same time 1 ml $5 \times 10^6$ A2780 human ovarian carcinoma cells are taken out from the first group of A2780 human ovarian carcinoma cells, and into which 100 μg chemotherapeutic drug of cisplatin is administrated;

1 ml $5 \times 10^6$ H22 mouse hepatoma cells are taken out from the second group of H22 mouse hepatoma cells and irradiated with UV for 30 minutes; at the same time 1 ml $5 \times 10^6$ A2780 human ovarian carcinoma cells are taken out from the second group of A2780 human ovarian carcinoma cells and irradiated with UV for 30 minutes;

the third group of H22 mouse hepatoma cells and the third group of the A2780 human ovarian carcinoma cells are left without any treatment.

3) 48 hours after the administration of chemotherapeutic drugs, the micro-particles (formed by wrapping the chemotherapeutic drug within the cell vesicles) derived from the first group of H22 mouse hepatoma cells and the first group of the A2780 human ovarian carcinoma cells are collected in accordance with the method of example 1, as a test group; 48 hours after the UV radiation, the cell vesicles derived from the second group of H22 mouse hepatoma cells and the second group of the A2780 human ovarian carcinoma cells are collected in accordance with the method of example 2 (no chemotherapeutic drug is wrapped therein), as a control group.

4) half of the micro-particles taken from the above test group, and half of the cell vesicles taken from the control group are respectively co-cultured with $5 \times 10^4$ tumor cells taken from the third group of tumor cells of different types for 72 hours within a 24-pore plate, the death of the tumor cells is observed, wherein the cell vesicles that are co-cultured with the tumor cells are the cell vesicles derived from the same type of tumor cells, and the micro-particles that are co-cultured with the tumor cells are the micro-particles formed after the cell vesicles derived from the same type of tumor cells have the chemotherapeutic drug wrapped therein;

At the same time, $5 \times 10^6$ H22 mouse hepatoma cells are taken out from the third group of H22 mouse hepatoma cells into which the pure chemotherapeutic drug of 10 μg methotrexate is administrated, and $5 \times 10^6$ A2780 human ovarian carcinoma cells are taken out from the third group of A2780 human ovarian carcinoma cells, into which 100 μg chemotherapeutic drug of cisplatin is administrated, after 72 hours of the administration, the death of the tumor cells is observed again.

3. Experimental Results

Figure 4:
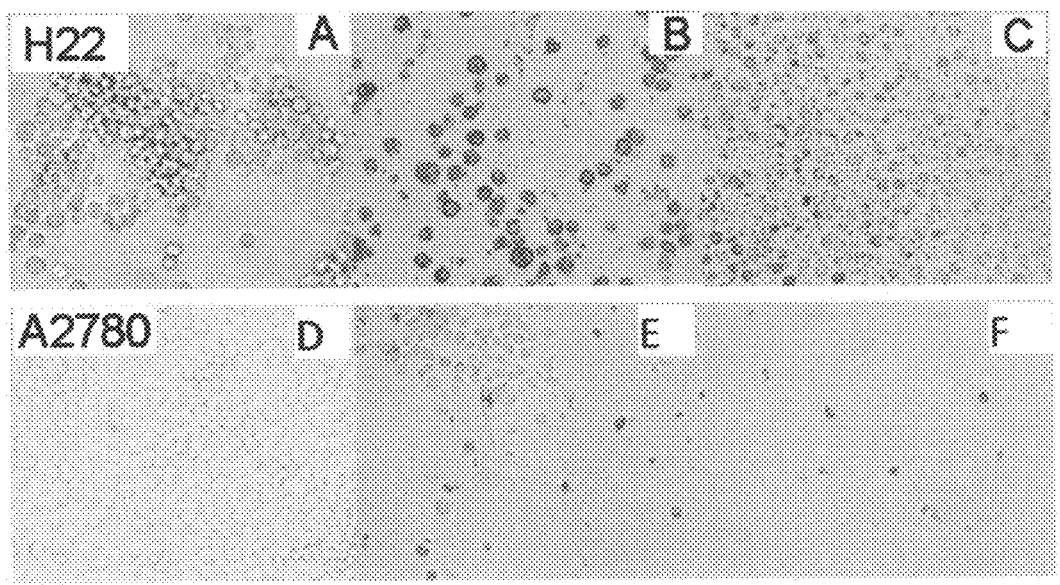
FIG. 4 shows that the micro-particles produced by inducing the hepatoma cell lines of mice with chemotherapeutic drugs have a significant killing effect against the hepatoma cells of mice after being absorbed.

These results show that, the cell vesicles of the control group not containing the chemotherapeutic drugs can't induce the death of the tumor cells (see FIG. 4A and FIG. 4D); although the pure chemotherapeutic drugs of methotrexate and cisplatin respectively kill H22 mouse hepatoma cells and A2780 human ovarian carcinoma cells, there are still certain amount of tumor cells survived (see FIG. 4B and FIG. 4E); while the micro-particles containing the chemotherapeutic drug can kill almost all tumor cells (see FIG. 4C and FIG. 4F), which proved that after administrating the pharmaceutical preparation for tumor chemotherapy of the present invention, whose main ingredients are micro-particles formed by wrapping the chemotherapeutic drug within the cell vesicles, to the tumor cells, the administration effects of the chemotherapeutic drugs acting as active ingredients are greatly enhanced.

Example 5

After Killing the Tumor Cells by Administrating Micro-Particles with Chemotherapeutic Drugs Wrapped Therein, Micro-Particles with Chemotherapeutic Drugs Wrapped Therein are Further Produced from the Killed Tumor Cells and Continue to Kill the Remaining Tumor Cells 1. Experimental Materials and Reagents H22 mouse hepatoma cells and A2780 human ovarian carcinoma cells used in example 5 are the same as example 1, and the chemotherapeutic drugs of methotrexate, cisplatin are commercially available.

2. Experimental Procedures

H22 mouse hepatoma cells and A2780 human ovarian carcinoma cells are cultured, so that their cell amount reaches $3 \times 10^8$, respectively, and the culture method is the same with example 1, the above obtained cell-culture medium of H22 mouse hepatoma cells is divided into three groups, each containing ⅓ cell amount of H22 mouse hepatoma cells; similarly, the cell-culture medium of the A2780 human ovarian carcinoma cells is divided into three groups, each containing ⅓ cell amount of A2780 human ovarian carcinoma cells.

2) On the first day, 10 ml $5 \times 10^7$ H22 mouse hepatoma cells are taken out from the first group of H22 mouse hepatoma cells and into which 100 μg chemotherapeutic drug of methotrexate is administrated; at the same time 10 ml $5 \times 10^7$ A2780 human ovarian carcinoma cells are taken out from the first group of A2780 human ovarian carcinoma cells, and into which 1000 μg chemotherapeutic drug of cisplatin is administrated;

10 ml $5 \times 10^7$ H22 mouse hepatoma cells are taken out from the second group of H22 mouse hepatoma cells and irradiated with UV for 30 minutes; at the same time 10 ml $5 \times 10^7$ A2780 human ovarian carcinoma cells are taken out from the second group of A2780 human ovarian carcinoma cells and irradiated with UV for 30 minutes;

the third group of H22 mouse hepatoma cells and the third group of the A2780 human ovarian carcinoma cells are left without any treatment.

3) 48 hours after the administration of chemotherapeutic drugs, the micro-particles (formed by wrapping the chemotherapeutic drugs within the cell vesicles) derived from the first group of H22 mouse hepatoma cells and the first group of the A2780 human ovarian carcinoma cells are collected in accordance with the method of example 1, as a test group; 48 hours after the UV radiation, the cell vesicles derived from the second group of H22 mouse hepatoma cells and the second group of the A2780 human ovarian carcinoma cells are collected in accordance with the method of example 2 (no chemotherapeutic drugs are wrapped therein), as a control group.

4) The micro-particles taken from the above test group, and the cell vesicles taken out from the control group are respectively co-cultured with the first batch of $5 \times 10^6$ H22 mouse hepatoma cells taken from the third group of H22 mouse hepatoma cells and first batch of $5 \times 10^6$ A2780 human ovarian carcinoma cells taken from the third group of A2780 human ovarian carcinoma cells for 12 hours within the 6-pore plate. After replacing the culture medium with a new culture medium, the culture was continued for 72 hours. New micro-particles of the test group and new cell vesicles of the control group are separated from the culture medium. The separated new micro-particles of the test group and new cell vesicles of the control group are respectively co-cultured with the second batch of $5 \times 10^4$ H22 mouse hepatoma cells taken from the third group of H22 mouse hepatoma cells and the second batch of $5 \times 10^4$ A2780 human ovarian carcinoma cells taken from the third group of A2780 human ovarian carcinoma cells within the 24-pore plate. The second batch of tumor cells into which micro-particles of the test group and the cell vesicles of the control group are administrated are respectively dyed with PI dye, then the death status of the tumor cells taken out for the second time is observed via flow cytometry, and the results are indicated in FIG. 5.

3. Experimental Results

Figure 5:
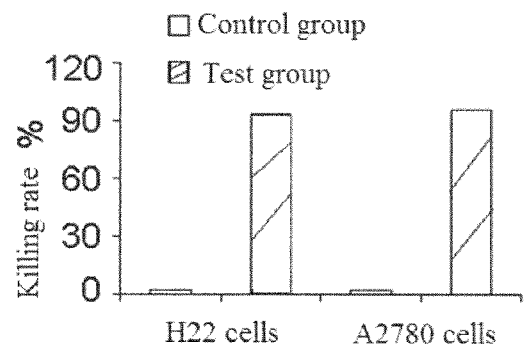
FIG. 5 shows that, after killing the tumor cells by administrating micro-particles with chemotherapeutic drugs wrapped therein, micro-particles with chemotherapeutic drugs wrapped therein are further produced from the killed tumor cells and continue to kill the remaining tumor cells.

As can be seen from FIG. 5, administrating new micro-particles of the test group to the tumor cells taken out for the second time still can kill 90% of the tumor cells, while administrating new cell vesicles of the control group substantially has no killing effect to the tumor cells, showing that the first batch of the tumor cells killed by the micro-particles of the test group (formed by wrapping the chemotherapeutic drugs within the cell vesicles) may further produce new micro-particles of the test group with chemotherapeutic drugs wrapped therein to continue killing the tumor cells taken out for the second time; while the cell vesicles of the control group without wrapping chemotherapeutic drugs do not have the above functions. The pharmaceutical preparation for tumor chemotherapy of the present invention has a continuous killing effect against the tumor cells. Based on the desired killing effects of the tumor cells and the types of tumor cells, those skilled in the art can appropriately choose the dosage of the chemotherapeutic drugs in accordance with the method as described in the present invention.

Example 6

The Experiment for Toxic Side-Effects of the Micro-Particles with Chemotherapeutic Drugs Wrapped Therein to the Organism 1. Experimental Materials and Reagents H22 mouse hepatoma cells and A2780 human ovarian carcinoma cells used in example 6 are the same with example 1, and the chemotherapeutic drugs of methotrexate, cisplatin are commercially available. 16 BALB/c mice and 16 severe combined immunodeficiency disease (SCID) mice purchased from Laboratory Animal Center, College of Medicine of Wuhan University.

2. Experimental Procedures

1) H22 mouse hepatoma cells and A2780 human ovarian carcinoma cells are cultured, so that their amount reaches $2 \times 10^7$, respectively, and the culture method is the same as example 1.

2) 1 ml $5 \times 10^6$ cell-culture medium of H22 mouse hepatoma cells is taken out from the above cultured cells, into which 100 μg chemotherapeutic drug of methotrexate is administrated; the cell-culture medium of 1 ml $5 \times 10^6$ A2780 human ovarian carcinoma cells is taken out, and into which 1000 μg chemotherapeutic drug of cisplatin is administrated.

3) 48 hours after administrating the chemotherapeutic drugs, the micro-particles (formed by wrapping the chemotherapeutic drugs within the cell vesicles) derived from H22 mouse hepatoma cells and from A2780 human ovarian carcinoma cells are collected in accordance with the method of example 1, and the amount of the micro-particles prepared from 1 ml of supernatant is stipulated as the dosage for 1 mouse.

4) The obtained micro-particles with the chemotherapeutic drug (methotrexate) wrapped therein of H22 mouse hepatoma cells are injected into 8 BALB/c mice through tail vein, respectively, as test group 1, and the obtained micro-particles with the chemotherapeutic drug (cisplatin) wrapped therein of A2780 human ovarian carcinoma cells are injected into 8 SCID mice through tail vein, respectively, as test group 2; at the same time, injecting 0.9% (g/ml) physiological saline into other 8 BALB/c mice and other 8 SCID mice, respectively, as control group 1 and control group 2; in the same operation and dosage, the test groups receive the injection of the micro-particles with chemotherapeutic drugs wrapped therein once a day for 14 days in succession, while the control groups receive the injection of 0.9% (g/ml) physiological saline once a day for 14 days in succession.

5) On the 15th day, venous blood of the test group 1, test group 2, control group 1 and control group 2 is gathered, respectively, the contents of glutamic-pyruvic transaminase (GPT) and creatinine in the blood serum are measured, the body weight of the mice is weighed.

3. Experimental Results

Figure 6A:
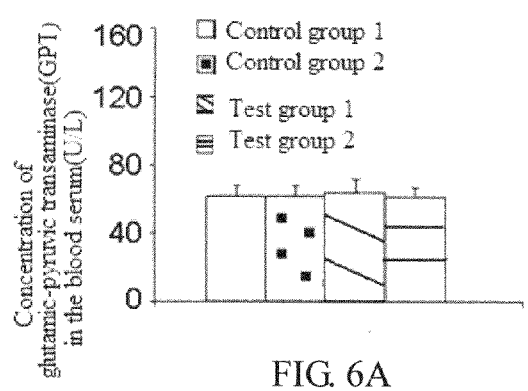
FIGS. 6A-6C show the toxic side-effects of the micro-particles with chemotherapeutic drugs wrapped therein against organism.
Figure 6B:
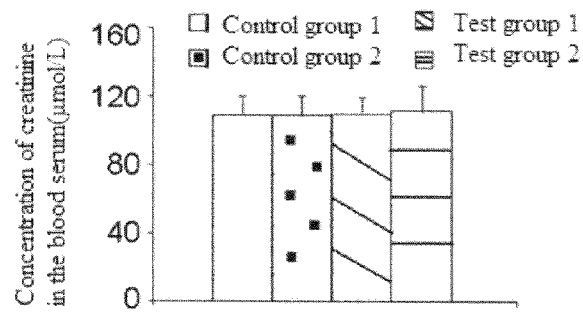
Figure 6C:
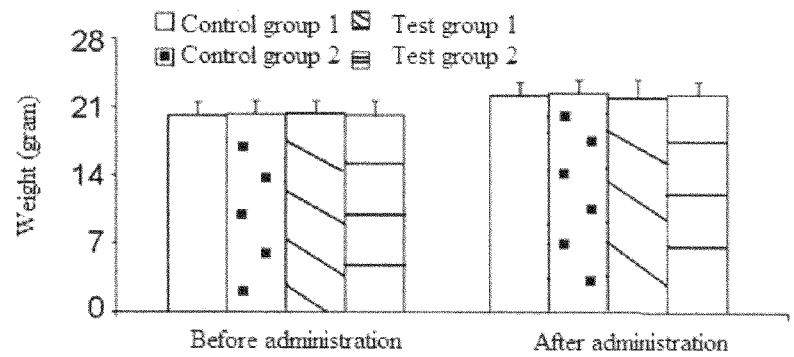

It can be seen from FIG. 6A-6C that, compared to the mice of the control group received the injection of physiological saline, the test group mice received the injection of micro-particles with the chemotherapeutic drug (methotrexate or cisplatin) wrapped therein, there is no significant change in the content of glutamic-pyruvic transaminase (GPT) and creatinine (see FIG. 6A and FIG. 6B) and the weight of the mice (see FIG. 6C). From this it can be perceived, using cell vesicles as carriers for the chemotherapeutic drugs, which will be wrapped in the cell vesicles to obtain the pharmaceutical preparation for tumor chemotherapy, substantially has no toxic side-effects to organism.

Example 7

The Growth of Tumors can be Inhibited by the Micro-Particles with Chemotherapeutic Drugs Wrapped Therein, and Prolonged Survival Time of Tumor-Bearing Mice can be Achieved 1. Experimental Materials and Reagents H22 mouse hepatoma cells and A2780 human ovarian carcinoma cells used in example 7 are the same with example 1, and the chemotherapeutic drugs of methotrexate, cisplatin are commercially available. BALB/c mouse and severe combined immunodeficiency disease SCID mouse.

2. Experimental Procedures

1) H22 mouse hepatoma cells and A2780 human ovarian carcinoma cells are cultured, so that their cell amount reaches $3\times10^7$, respectively, and the culture method is the same with example 1.

2) from the above cultured cells, 1 ml $5\times10^6$ H22 mouse hepatoma cells (with culture medium) are taken out, into which 100 µg chemotherapeutic drug of methotrexate is administrated; 1 ml $5\times10^6$ A2780 human ovarian carcinoma cells (with culture medium) are taken out, and into which 1000 µg chemotherapeutic drug of cisplatin is administrated; 48 hours after administrating the chemotherapeutic drugs, the micro-particles (formed by wrapping the chemotherapeutic drugs within the cell vesicles) derived from H22 mouse hepatoma cells and the A2780 human ovarian carcinoma cells are collected in accordance with the method of example 1, and the amount of the micro-particles prepared from 1 ml of supernatant is stipulated as the dosage for 1 mouse.

From the above cultured cells 1 ml $5\times10^6$ H22 mouse hepatoma cells (with culture medium), and 1 ml $5\times10^6$ A2780 human ovarian carcinoma cells (with culture medium) are taken out, 48 hours after they are exposed to UV radiation, the cell vesicles (without chemotherapeutic drugs wrapped therein) derived from H22 mouse hepatoma cells and the A2780 human ovarian carcinoma cells are collected respectively in accordance with the method of example 2, and the amount is stipulated as the dosage for 1 mouse.

3) On the first day, from the above cultured cells $1\times10^5$ H22 mouse hepatoma cells are taken out and injected into BALB/c mice by intraperitoneal injection, 32 mice in total; the BALB/c mice suffering from the ascitic tumor of H22 mouse hepatoma cells are randomly divided into two groups with same quantity; from the above cultured cells $1\times10^6$ A2780 human ovarian carcinoma cells are taken out and injected into SCID mice via intraperitoneal injection, 32 mice in total; the SCID mice suffering from ovarian tumor are randomly divided into two groups with same quantity.

4) From the second day, the micro-particles derived from H22 mouse hepatoma cells prepared in step 2) are injected into the first group of BALB/c mice with liver tumor obtained in step 3) at a certain amount of dosage via intraperitoneal injection, once a day for 7 days, and from the 8th day, the micro-particles injected BALB/c mice with liver tumor are normally fed, as a test group; for the second group of BALB/c mice with liver tumor, the cell vesicles prepared in step 2) are injected once a day for 7 days, and from the 8th day, the cell vesicles injected BALB/c mice with liver tumor are normally fed, as a control group;

Similarly, from the second day, the micro-particles derived from A2780 human ovarian carcinoma cells prepared in step 2) are injected into the first group of SCID mice with ovarian tumor obtained in step 3) at a certain amount of dosage via intraperitoneal injection once a day for 7 days, and from the 8th day, the micro-particles injected BALB/c mice with liver tumor are normally fed, as a test group; for the second group of SCID mice with ovarian tumor, the cell vesicles prepared in step 2) are injected once a day for 7 days, and from the 8th day, the cell vesicles injected BALB/c mice with liver tumor are normally fed, as a control group.

3. Experimental Results

Figure 7A:
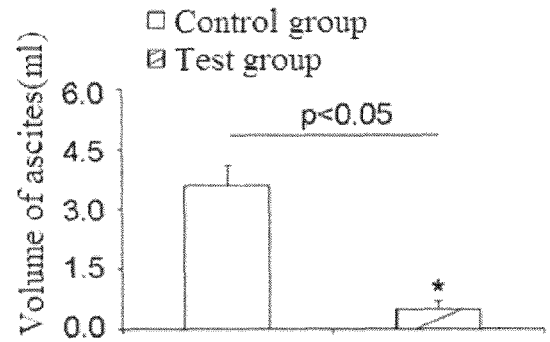
FIGS. 7A-7D show that the growth of tumors can be inhibited by the micro-particles with chemotherapeutic drugs wrapped therein, and prolonged survival time of tumor-bearing mice is achieved.
Figure 7B:
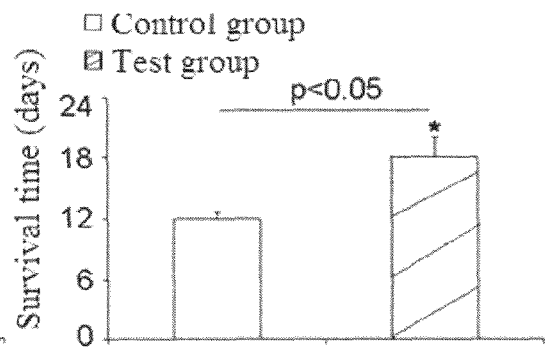
Figure 7C:
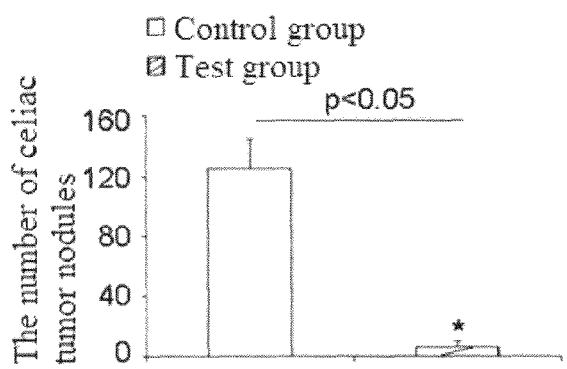
Figure 7D:
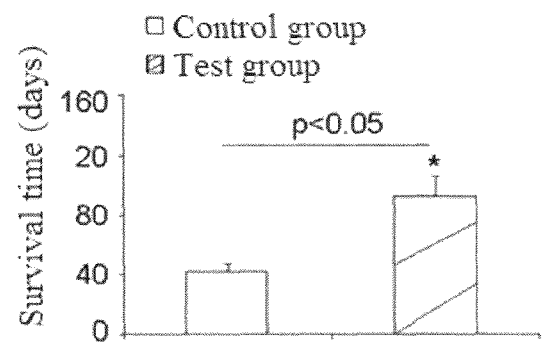

The BALB/c mice of the test and control groups are divided into two groups with the same amount, the first group BALB/c mice of the test group and the first group BALB/c mice of the control group are executed on the 10th day, respectively, their volume of ascites are measured (FIG. 7A), the second group BALB/c mice of the test group and the second group BALB/c mice of the control group are respectively used to observe survival time (FIG. 7B);

the SCID mice of the test group and control group are divided into two groups with the same amount, the first group SCID mice of the test group and the first group SCID mice of the control group are executed on the 30th day, the formed celiac tumor nodules are measured (FIG. 7C), the second group SCID mice of the test group and the second group SCID mice of the control group are respectively used to observe survival time (FIG. 7D).

The results show that, compared to the control group, in the test group, the growth of H22 mouse hepatoma cells of the BALB/c mice has been significantly inhibited by the micro-particles with methotrexate wrapped therein derived from H22 mouse hepatoma cells, and prolonged survival time of the BALB/c mice has been achieved; similarly, the growth of A2780 ovarian tumor cells of the SCID mice has been significantly inhibited by the micro-particles with cisplatin wrapped therein derived from A2780 ovarian tumor cells, and prolonged survival time of the SCID mice has been achieved.

Example 8

Application of the Technical Solutions of the Present Invention to Tumor Cells of Other Types 1. Experimental Materials and Reagents Different tumor cell lines comprise: human breast tumor cell line MCF-7, human lung carcinoma cells A549, human gastric tumor cell line SNU1, human colonic tumor Caco-2, human hepatoma cell line HepG2, human bladder tumor cell line T24, human leukemia cell line K562, as well as human glioma cell line U 251;

The chemotherapeutic drug of methotrexate is commercially available.

2. Experimental Procedures

1) Culturing the above types of tumor cell lines in the DMEN culture medium, such that each type of tumor cell lines has the cell amount of $2\times10^8$, respectively, and each type of the cultured tumor cell lines is divided into two groups.

2) For the first group, 100 µg chemotherapeutic drug of methotrexate is respectively added into 10 ml $5\times10^7$ culture medium of each type of the cultured tumor cells, and the micro-particles (formed by wrapping the chemotherapeutic drugs within the cell vesicles) containing methotrexate derived from the each type of the tumor cells are obtained; for the second group, 10 ml $5\times10^7$ of each type of tumor cells are exposed to UV radiation for 30 minutes, the cell vesicles not containing methotrexate and derived from each type of the tumor cells are obtained.

3) 48 hours after administrating the chemotherapeutic drug, the micro-particles derived from the first group of each type of the tumor cell lines are collected in accordance with the method of example 1, as a test group; the cell vesicles derived from the second group of each type of the tumor cell lines are collected in accordance with the method of example 2, as a control group.

Figure 8:
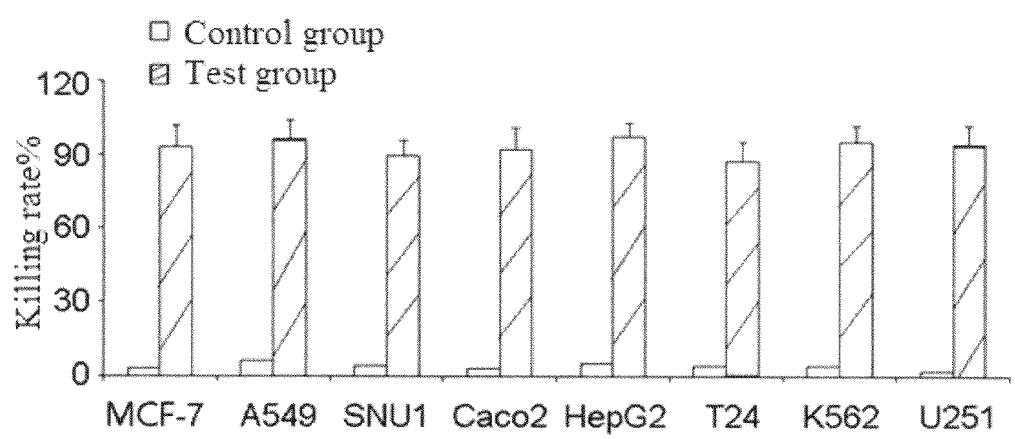
FIG. 8 shows the application of the technical solution of the present invention to other tumor cells.

4) The prepared half of the test group micro-particles and half of the control group cell vesicles are respectively co-cultured with the corresponding $5\times10^6$ tumor cells within a 6-pore plate for 72 hours, the tumor cells into which the test group micro-particles are administrated and the tumor cells into which the cell vesicles of the control group are administrated are dyed with PI dye, respectively, the method of dyeing is the same with example 5, then the death status of the different types of tumor cells is observed via flow cytometry, and the results are indicated as FIG. 8.

3. Experimental Results

It can be seen from FIG. 8 that, the micro-particles with chemotherapeutic drugs wrapped therein derived from different types of tumor cells can kill approximately 90% tumor cells where they derived from, which indicates that the pharmaceutical preparation for tumor chemotherapy and the method for producing the same provided by the present invention are applicable to various tumor cells, and better chemotherapy effects can be achieved.

Example 9

The Micro-Particles with Chemotherapeutic Drugs Wrapped Therein can be Targeted to the Solid Tumor Through the Blood 1. Experimental Materials and Reagents H22 mouse hepatoma cells use in example 9 are the same with example 1, the chemotherapeutic drugs of Adriamycin and BALB/c mice both are commercially available.

2. Experimental Procedures

H22 mouse hepatoma cells are cultured to reach the cell amount of $3 \times 10^7$, the culture medium of above H22 mouse hepatoma cells is divided into two groups, each group containing half cell amount of H22 mouse hepatoma cells; similarly, the culture medium of A2780 human ovarian carcinoma cells is divided into two groups, each group containing half cell amount of A2780 human ovarian carcinoma cells.

2) From the first group of H22 mouse hepatoma cells (with the culture medium), 1 ml $1 \times 10^7$ cell-culture medium of H22 mouse hepatoma cells are taken out, into which 300 μg the chemotherapeutic drug of adriamycin is administrated; 48 hours after administrating the chemotherapeutic drug, the micro-particles (cell vesicles with chemotherapeutic drug wrapped therein) derived from H22 mouse hepatoma cells are collected in accordance with the method of example 1, and the amount of the micro-particles prepared from 1 ml of supernatant is stipulated as the dosage for 1 mouse.

From the second group of H22 mouse hepatoma cells (with culture medium), 1 ml $1 \times 10^7$ H22 mouse hepatoma cells are taken out, 48 hours after they are exposed to UV radiation, cell vesicles (without wrapping chemotherapeutic drug therein) of H22 mouse hepatoma cells are collected in accordance with the method of example 2, as a control group, and the amount is stipulated as the dosage for 1 mouse.

3) On the first day, $2 \times 10^5$ H22 mouse hepatoma cells are subcutaneously inoculated to 12 BALB/c mice, respectively, and the BALB/c mice suffering from subcutaneous liver tumor are obtained and divided into two groups randomly.

4) From the 15th day, the micro-particles derived from the first group of H22 mouse hepatoma cells prepared in step 2) are injected into the first group of BALB/c mouse with liver tumor obtained in step 3) at a certain amount of dosage through tail vein, as a test group; and the cell vesicles derived from the second group of H22 mouse hepatoma cells prepared in step 2) are injected into the second group of BALB/c mouse with liver tumor through tail vein, as a control group; 6 hours later, upon frozen section the tumor tissues are observed by fluorescence microscope.

3. Experimental Results

Figure 9:
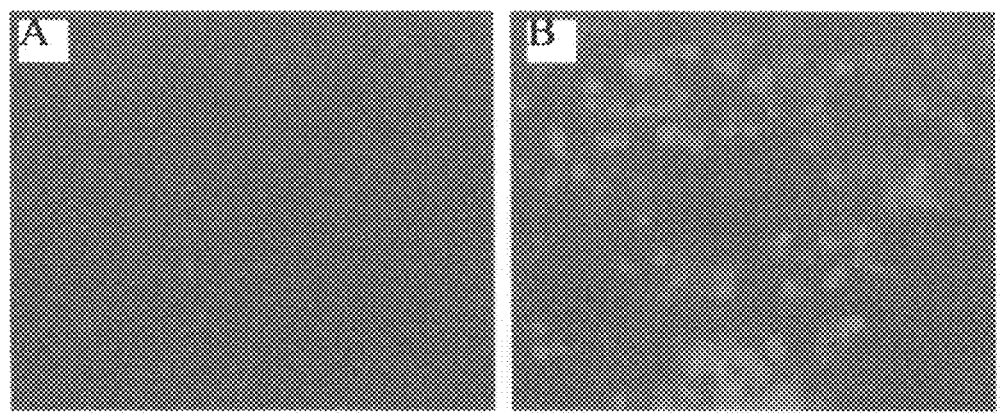
FIG. 9 shows that the micro-particles with chemotherapeutic drugs wrapped therein can be targeted to the solid tumor through blood.

It can be seen from FIGS. 9A-9B that, the micro-particles with adriamycin wrapped therein derived from the first group of H22 mouse hepatoma cells are targeted to the tumor tissues through the blood, showing red color (as indicated in FIG. 9B), while the tumor tissues into which the cell vesicles derived from the second group of H22 mouse hepatoma cells are injected don't show any fluorescence (as indicated in FIG. 9A), which proves the micro-particles with adriamycin wrapped therein provided by the present invention can act as a targeted drug to selectively locate the tumor sites and kill the tumor.

What is claimed is:

1. A pharmaceutical preparation for tumor chemotherapy comprising: cell vesicles derived from apoptotic tumor cells and chemotherapeutic drugs wrapped within the cell vesicles acting as active ingredient, wherein the cell vesicles are obtained by: centrifuging cell culture medium that contains apoptotic tumor cells and collecting a first supernatant; centrifuging the first supernatant at a centrifugal force of not more than 14000 g so as to remove cells and debris, and collecting a second supernatant; further centrifuging the second supernatant at a centrifugal force of 14,000 g-100,000 g to obtain the cell vesicles, the chemotherapeutic drugs are methotrexate and cisplatin and, the vesicles are derived from mouse hepatoma and human ovarian carcinoma cells.

2. The pharmaceutical preparation for tumor chemotherapy according to claim 1, wherein the pharmaceutical preparation form for tumor chemotherapy comprises an injection preparation.

3. The pharmaceutical preparation for tumor chemotherapy according to claim 1, wherein the granularity of the pharmaceutical preparation for tumor chemotherapy formed by wrapping the chemotherapeutic drugs within the cell vesicles is 100-1000 nm.

4. A method for producing the pharmaceutical preparation for tumor chemotherapy according to claim 1, comprising:
   administrating the chemotherapeutic drugs as active ingredient to tumor cells to induce apoptosis of the tumor cells, and collecting micro-particles released from the apoptotic tumor cells, wherein the micro-particles are the pharmaceutical preparation formed after wrapping the chemotherapeutic drugs within the cell vesicles; or
   using UV to irradiate the tumor cells to induce apoptosis, collecting the cell vesicles released by the apoptotic tumor cells, then incubating the cell vesicles with the chemotherapeutic drugs acting as active ingredient, wrapping the chemotherapeutic drugs within the cell vesicles, and collecting micro-particles, wherein the micro-particles are the pharmaceutical preparation formed after wrapping the chemotherapeutic drugs within the cell vesicles.

5. The method for producing a pharmaceutical preparation for the tumor chemotherapy according to claim 4, further comprising culturing the tumor cells before inducing the apoptosis of the tumor cells by administrating the chemotherapeutic drugs acting as active ingredient or by UV radiation.

6. A method for treating tumors, comprising performing chemotherapy through the administration of the pharmaceutical preparation for tumor chemotherapy according to claim 1 to the patients with tumors.

7. A method for treating tumors according to claim 6, wherein the pharmaceutical preparation form for tumor chemotherapy comprises an injection preparation.

8. A method for treating tumors according to claim 6, wherein the granularity of the pharmaceutical preparation for tumor chemotherapy formed by wrapping the chemotherapeutic drugs within the cell vesicles is 100-1000 nm.

* * * * *